(12) United States Patent
Suzuki

(10) Patent No.: US 7,967,819 B2
(45) Date of Patent: Jun. 28, 2011

(54) SOFT BIPOLAR FORCEPS

(75) Inventor: Keita Suzuki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1124 days.

(21) Appl. No.: 11/731,721

(22) Filed: Mar. 30, 2007

(65) Prior Publication Data

US 2007/0244480 A1 Oct. 18, 2007

(30) Foreign Application Priority Data

Apr. 17, 2006 (JP) ................. 2006-113401

(51) Int. Cl.
*A61B 18/14* (2006.01)
(52) U.S. Cl. ................ 606/48; 606/51; 606/52
(58) Field of Classification Search .......... 606/51, 606/52, 48
See application file for complete search history.

(56) References Cited

U.S. PATENT DOCUMENTS

| 2001/0037109 A1 | 11/2001 | Yamauchi et al. |
| 2003/0120268 A1 | 6/2003 | Bertolero et al. |

FOREIGN PATENT DOCUMENTS

| EP | 1 350 480 A1 | 10/2003 |
| GB | 2 321 015 A | 7/1998 |
| JP | 05-253241 | 10/1993 |
| JP | 11-033033 | 2/1999 |
| JP | 11-128240 | 5/1999 |

*Primary Examiner* — Lee S Cohen
(74) *Attorney, Agent, or Firm* — Scully, Scott, Murphy & Presser, P.C.

(57) ABSTRACT

A soft bipolar forceps includes a long narrow flexible tube; paired forceps pieces that are formed extending in the axial direction, and are mutually insulated and disposed opposite one another; and a support that is disposed to the distal end of the flexible tube and supports the paired forceps pieces to permit relatively free opening and closing thereof; characterized in that a first electrode is disposed to one of the paired forceps pieces, a second electrode is disposed to the other of the paired forceps pieces opposite the first electrode, and a guide part that extends to permits elastic deformation is disposed to the distal end of the first electrode.

6 Claims, 7 Drawing Sheets

SOFT BIPOLAR FORCEPS

BACKGROUND OF THE INVENTION

1. Field of the Invention

The present invention relates to a soft bipolar forceps.

Priority is claimed on Japanese Patent Application No. 2006-113401, filed Apr. 17, 2006, the content of which is incorporated herein by reference.

2. Description of Related Art

Endoscopic procedures are being used increasingly in the treatment of diseases of the digestive and pancreatobiliary systems. Procedures performed on the pancreatobiliary system that employ conventional endoscopes include therapeutic procedures, such as the retrieval of choleoliths present in biliary ducts using a balloon or grasping tool, as well as diagnostic procedures for endoscopic visualization of the pancreatic or biliary ducts.

When performing such endoscopic procedures on the pancreatic, biliary, or hepatic ducts, the distal end of the inserted portion of the endoscope is inserted as far as the proximity of the duodenal papilla. From this point, the guide wire disposed in the contrast catheter is employed as a guide to insert a papillotomy knife into either the pancreatic or biliary duct selectively under fluoroscopy, and a duodenal papillotomy for opening the duodenal papilla is carried out. (See, for example: Japanese Patent Application, First Publication No. Hei 11-033033, Japanese Patent Application, First Publication No. Hei 11-128240).

In addition, in place of a papillotomy knife, it is also possible to employ a high-frequency forceps that is able to incise the subject tissue only when the paired forceps pieces are closed, each of these paired pieces having a cutting electrode and a recovery electrode disposed respectively therein (for example, see: Japanese Patent Application, First Publication No. Hei 05-253241).

SUMMARY OF THE INVENTION

The present invention was conceived in view of the above-described circumstances and employs the following means.

The soft bipolar forceps according to the present invention is provided with a long narrow flexible tube; a pair of forceps pieces that are formed extending in the axial direction, and are mutually insulated and disposed opposite one another; and a support that is disposed to the distal end of the flexible tube and supports the paired forceps pieces to permit relatively free opening and closing thereof; characterized in that a first electrode is disposed to one of the paired forceps pieces, a second electrode is disposed to the other of the paired forceps pieces opposite the first electrode, and a guide part that extends in the axial direction and permits elastic deformation is disposed to the distal end of the first electrode.

The soft bipolar forceps according to the present invention is further characterized in that a through hole is provided in the axial direction of the guide part in the above-described soft bipolar forceps.

The soft bipolar forceps according to the present invention is further characterized in that, in the soft bipolar forceps as described above, the guide part is provided with conductive properties.

The soft bipolar forceps according to the present invention is further characterized in that, in the soft bipolar forceps as described above, the first electrode is formed in a unitary manner with the guide part in a manner that enables elastic deformation.

The soft bipolar forceps according to the present invention is further characterized in that, in the soft bipolar forceps as described above, an insulating part for electrically insulating between the paired forceps pieces is disposed to the aforementioned support.

The soft bipolar forceps according to the present invention are further characterized in that, in the soft bipolar forceps as described above, the insulating part which electrically insulates between the paired forceps pieces is disposed to the respective base ends of the paired forceps pieces.

DETAILED DESCRIPTION OF THE INVENTION

A first embodiment of the present invention will now be explained with reference to FIGS. 1 through 4.

Figure 1:
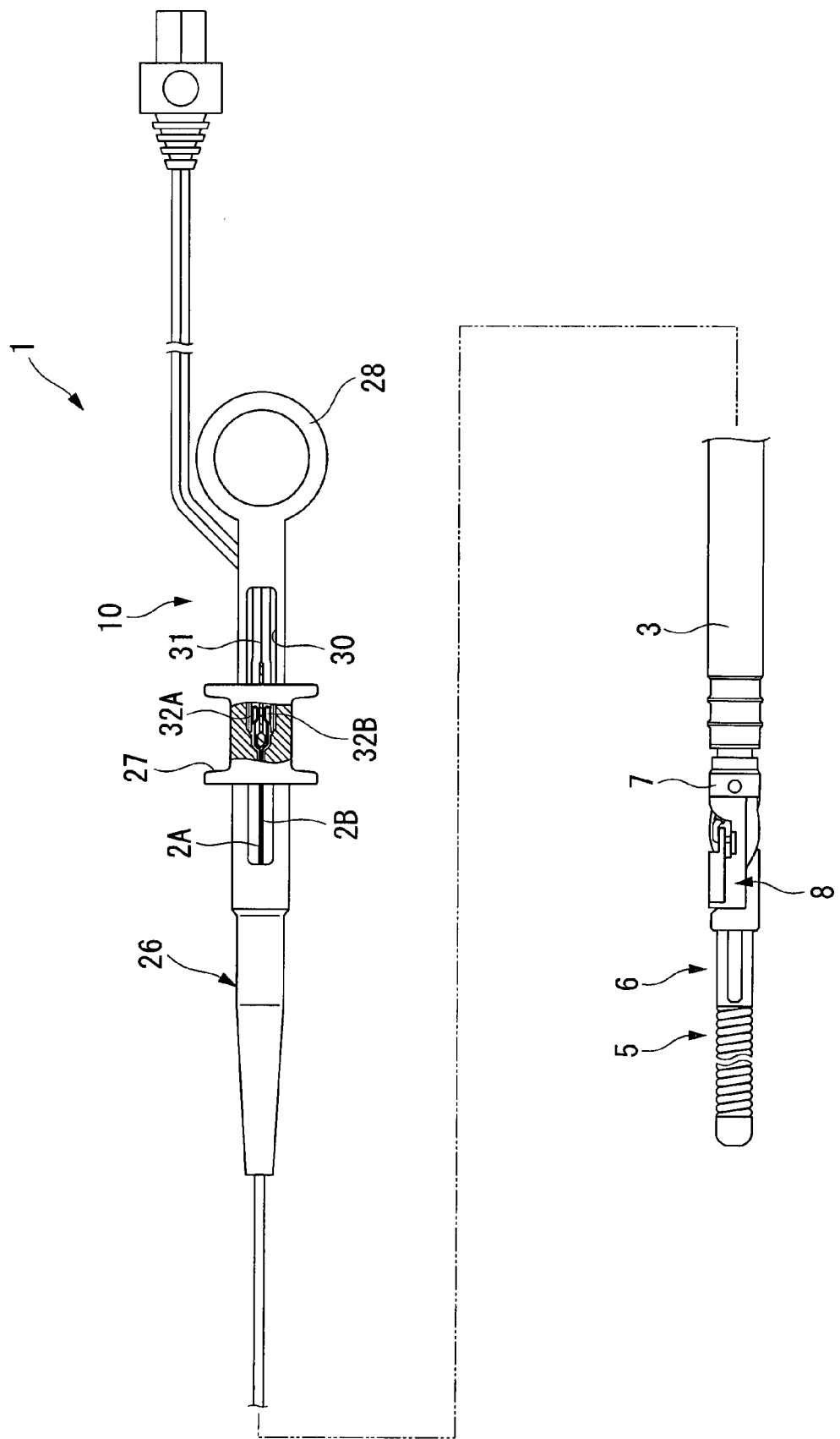
FIG. 1 is a schematic view of the entire soft bipolar forceps according to the first embodiment of the present invention.

As shown in the FIG. 1, in the soft bipolar forceps 1 according to this embodiment, a long narrow flexible tube 3, into which a pair of operating wires 2A, 2B have been inserted, and a pair of forceps pieces 5, 6, which are formed extending in the axial direction and are mutually insulated and disposed opposite one another, are connected to the distal end of flexible tube 3 via a connecting member 7. Soft bipolar forceps 1 is further provided with a tip cover (support) 8 for supporting the paired forceps pieces 5, 6 to permit relatively free opening or closing thereof, and an operator 10 for advancing or retracting the paired operating wires 2A, 2B with respect to flexible tube 3.

Figure 2:
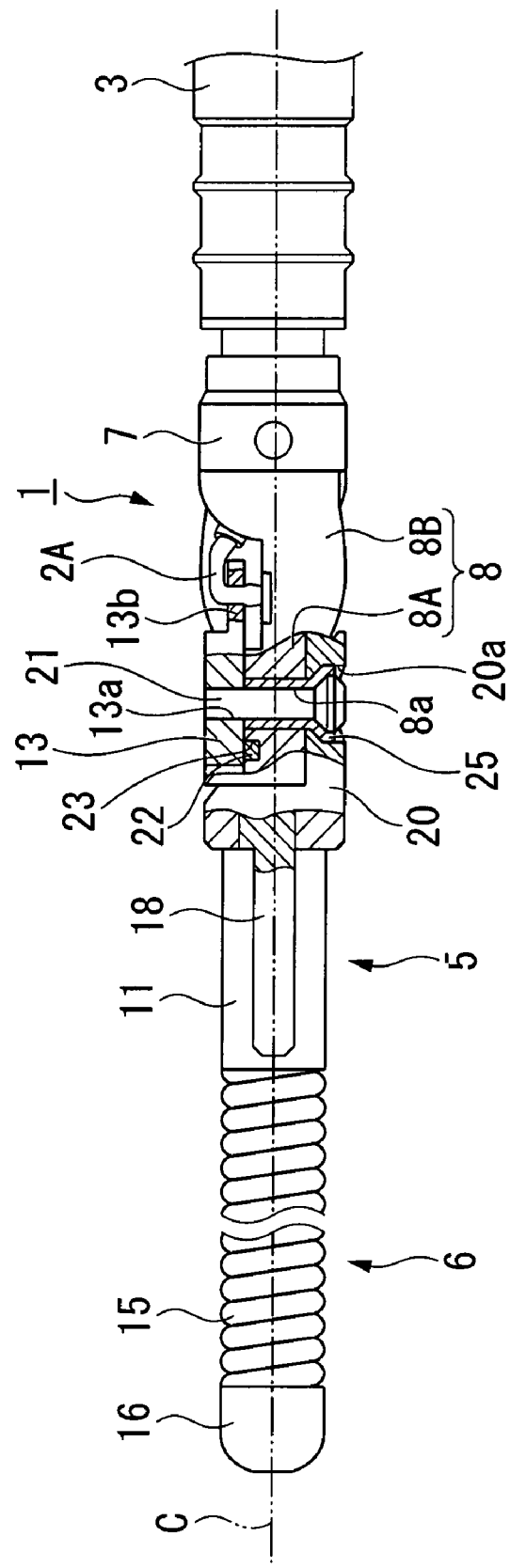
FIG. 2 is an essential component plan view that includes a cross-section through a portion of the soft bipolar forceps according to the first embodiment of the present invention.
Figure 3:
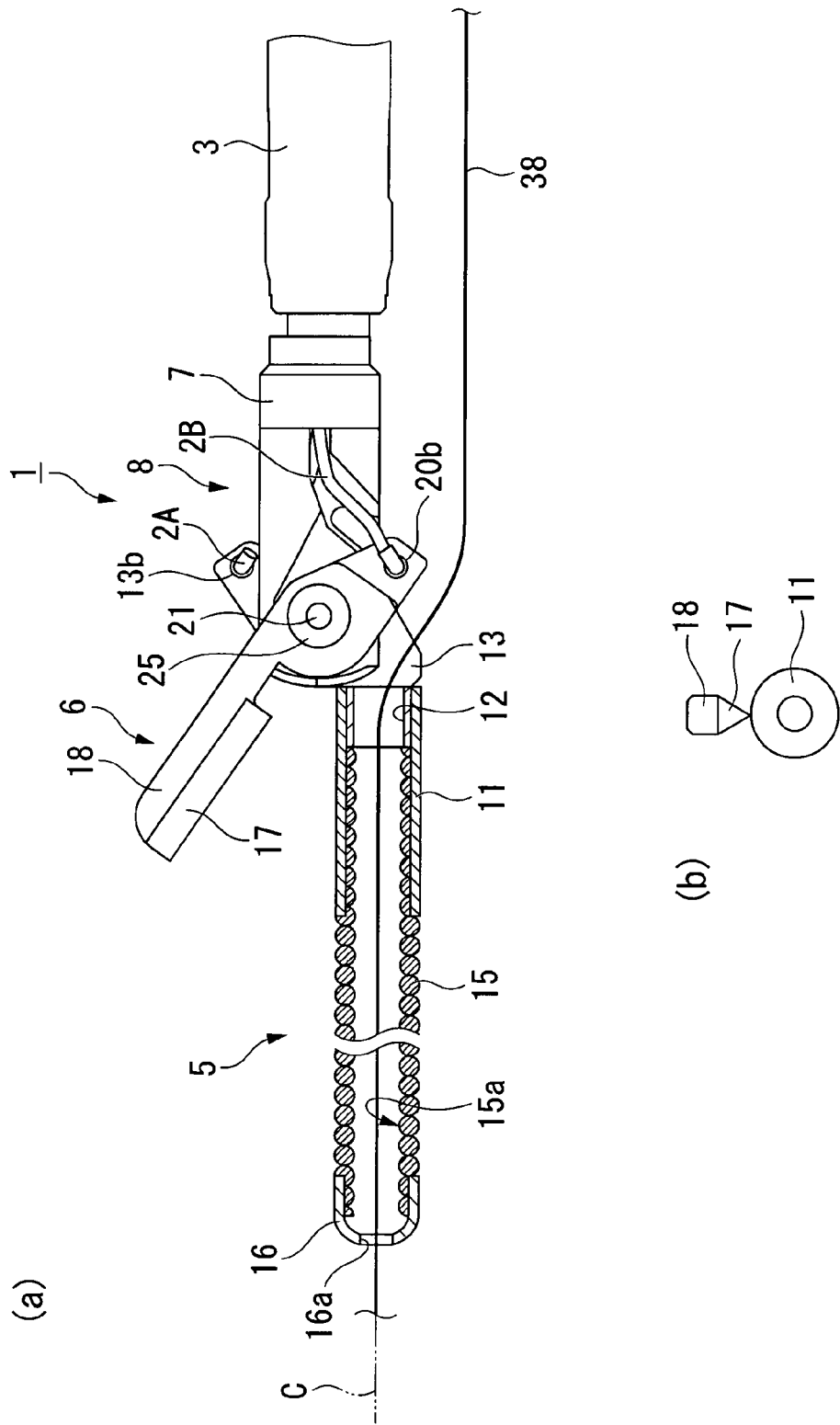
FIG. 3 is an essential component side view that includes a cross-section through a portion of the soft bipolar forceps according to the first embodiment of the present invention.

A first electrode 11 which is formed of stainless steel and is in the shape of a straight tube is disposed to the forceps piece 5. As shown in FIGS. 2 and 3, the first electrode 11 is formed to permit engagement at its distal end with the outer peripheral surface of the forceps piece 5. The forceps piece 5 is provided with a first arm 12, a first connector 13 and a guide part 15. The first arm 12 extends along the center axis C of the forceps piece 5. The first connector 13 moves away from the center axis C in the cross direction with respect to the first arm 12 and bends. After moving a set distance away from the center axis C, this first connector 13 bends again to extend along the center axis C direction. The guide part 15 extends in the axial direction and is designed to enable elastic deformation at the distal end of the first electrode 11. A first through hole 13a is formed in the approximate center of the first connector 13 to permit passage through the first connector 13 in the cross direction. A conductive part 13b is provided to the base end of the first connector 13, and the operating wire 2A is connected thereto.

The guide part 15 extends linearly from the first electrode 11 in the axial direction, and has a through hole 15a. This guide part 15 is designed to be in the form of a stainless steel coil that is elastically deformable, and can engage with the inner peripheral surface of the distal end side of the first electrode 11. An end tip 16 in which a hole 16a is provided that communicates with the through hole 15a is disposed at the end of the guide part 15.

A second electrode 17 is disposed opposite the first electrode 11 and serves as a different terminal than the first electrode 11. This second electrode 17 is approximately the same length as the first electrode 11 and is formed to have a roughly triangular shape in cross-section such that the width gradually narrows in the direction of the forceps piece 5 side. In other words, when the pair of forceps pieces 5, 6 are closed, the first electrode 11 and the second electrode 17 are designed to form a linear connection.

The forceps piece 6 is further provided with a second arm 18 that extends further than the first arm 12, and a second connector 20 bends in a direction away from the first arm 12, from the center axis C in the cross direction with respect to the second arm 18. After moving a set distance away from the center axis C, this second connector 20 bends again to extend along the center axis C direction. The second electrode 17 is disposed to the second arm 18. A second through hole 20a is formed in the approximate center of the second connector 20 to permit passage through the second connector 20 in the cross direction. A conductive part 20b is provided to the base end of the second connector 20, and the operating wire 2B is connected thereto.

Tip cover 8 consists of an insulated member formed of a ceramic such as zirconia, alumina or the like, or a resin such as polyetherether ketone (PEEK), polytetrafluoroethylene (PTFE), or polysulfone. Alternatively, tip cover 8 may consist of a member in which an insulating coating is applied to a stainless surface. The tip cover 8 is provided with a projecting part 8A that extends along the center axis C direction, and a base part 8B which is connected to the connecting member 7. A third through hole 8a which communicates with the first through hole 13a and the second through hole 20a is provided in the cross direction in the center of projecting part 8A. Further, the first connector 13 and the second connector 20 which are disposed on either side of projecting part 8A are connected in a freely rotating manner about a pivot support pin 21.

Stop pin 22 which is projecting out in the cross direction is provided to the first connector 13. The first connector 13 is engaged by the stop pin 22 in an engaging hole 23 formed in the projecting part 8A. As a result, relative movement of forceps piece 5 and tip cover 8 is restricted even if operating wire 2A is advanced or retracted. On the other hand, the second connector 20 rotates around the pivot support pin 21 by advancing or retracting the operating wire 2B, so that the second arm 18 can be opened or closed with respect to the first arm 12.

The first connector 13, the pivot support pin 21, the projecting part 8A and the second connector 20 are electrically insulated by an insulating spacer (insulating part) 25. In other words, the first electrode 11 and the second electrode 17 are electrically insulated by the insulating spacer 25.

The operator 10 is provided with a long, narrow operator main body 26 and a slider 27 which is disposed in a freely advancing and retracting manner with respect to the operator main body 26. A ring 28 for hooking the finger is provided to the base end of the operator main body 26. A slit 30 is provided further toward the front of the operator main body 26 than the ring 28. A pair of operating wires 2A, 2B are inserted into the operator main body 26. A pair of electrical terminals 32A, 32B to which a power source cord 31 is connected are embedded in the slider 27. The base end side of the operating wire 2A enters a state of connection with electrical terminal 32A by means of the advance and retraction of the slider 27, while the base end of the operating wire 2B is in a fixed connection with electrical terminal 32B.

Next, using a duodenal papillotomy as an example, an operation using the soft bipolar forceps 1 according to this embodiment will be explained.

First, the inserted part 35 of the endoscope 33 is inserted into the body cavity and disposed near the duodenal papilla 36. Then, the soft bipolar forceps 1 is inserted into the instrument insertion channel 37 that is provided in the inserted part 35, and is made to project out from the distal end of the inserted part 35 in the direction of the biliary duct 39. At this point, the guide wire 38, previously inserted into the instrument insertion channel 37 by a specific method, is inserted into the forceps piece 5 and made to project out. Power source cord 31 is connected to a high frequency power source not shown in the figures. Here, operating wire 2A is the positive electrode and operating wire 2B is the negative electrode.

When carrying out a procedure, the finger is suspended in the slider 27 and the ring 28 of the operator main body 26, the slider 27 is advanced, and the operating wire 2B is advanced with respect to the flexible tube 3. At this time, the base end of the forceps piece 6 is pushed in the forward direction of the operator main body 26 by the operating wire 2B, causing the forceps piece 6 to rotate about the pivot support pin 21 in a direction away from the forceps piece 5.

Figure 4:
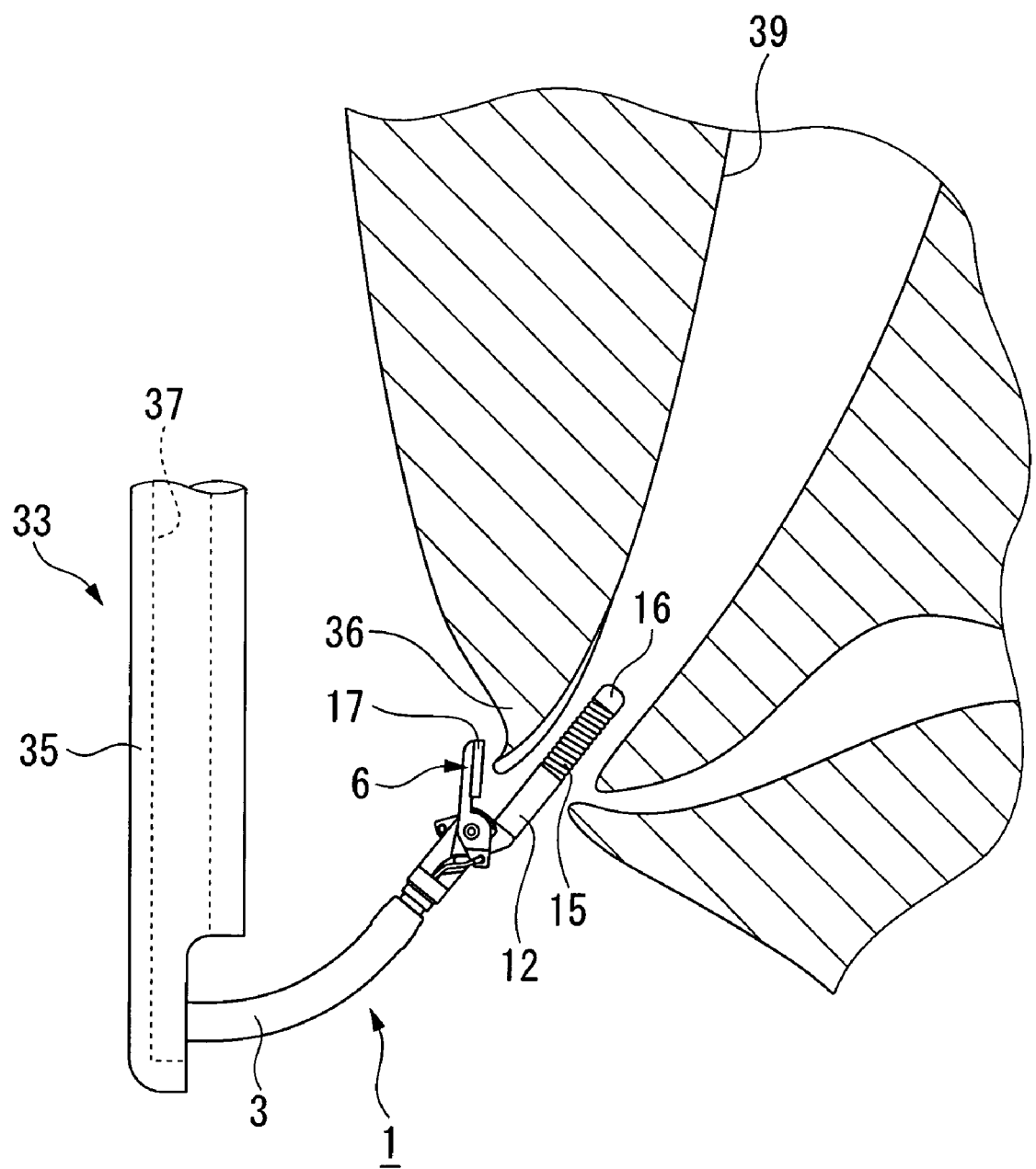
FIG. 4 is an explanatory figure showing the arrangement for use of the soft bipolar forceps according to a first embodiment of the present invention.

In this state, the inserted part 35 and the entirety of the soft bipolar forceps 1 is advanced, and the guide part 15 is inserted into the biliary duct 39, to enter the state shown in FIG. 4. In this case, since the guide part 15 is elastically deformable, it undergoes bending and can be inserted smoothly into the biliary duct 39. Once the forceps pieces 5 has been inserted to a position that enables gripping of the diseased area between the first electrode 11 and the second electrode 17, the slider 27 is retracted with respect to the operator main body 26. The operating wire 2B is retracted at this time, and the forceps piece 6 is rotated about the pivot support pin 21 so that the second arm 18 approaches the first arm 12, and a specific diseased area such as the papilla 36 that is to be incised is held between the first electrode 11 and the second electrode 17.

By activating the high frequency power source, electrical energy is supplied to the first electrode 11 and the second electrode 17 via the paired operating wires 2A, 2B, and current is passed through the diseased area to incise it. Once the procedure is done, supply from the high-frequency power source is stopped. Slider 27 is retracted and the grip on the diseased area is released by rotating the forceps piece 6 around the pivot support pin 21 in the direction away from the forceps piece 5, and the flexible bipolar forceps 1 is withdrawn from the body together with the inserted part 35.

In this soft bipolar forceps 1, the guide part 15 is inserted into such as the hepatic duct 39, and, in this state of insertion, the diseased area is gripped by the paired forceps pieces 5, 6. Current from the high-frequency power source is then passed between the first electrode 11 and the second electrode 17. Accordingly, the diseased area can be incised in a stable manner using the soft bipolar forceps 1 of the present invention. Moreover, since the guide part 15 is elastically deformable, it can be inserted easily into the hepatic duct 39. Accordingly, the duration of the procedure can be shortened.

Instruments such as the guide wire 38, etc., required for the procedure can be inserted into the forceps 5 piece, and the soft bipolar forceps 1 can be moved using through hole 15a. Since the guide part 15 also possesses conductivity, the guide part 15 and the first electrode 11 enter a state of conductivity, so that current can flow between the guide part 15 and the second electrode 17 as well.

Figure 5:
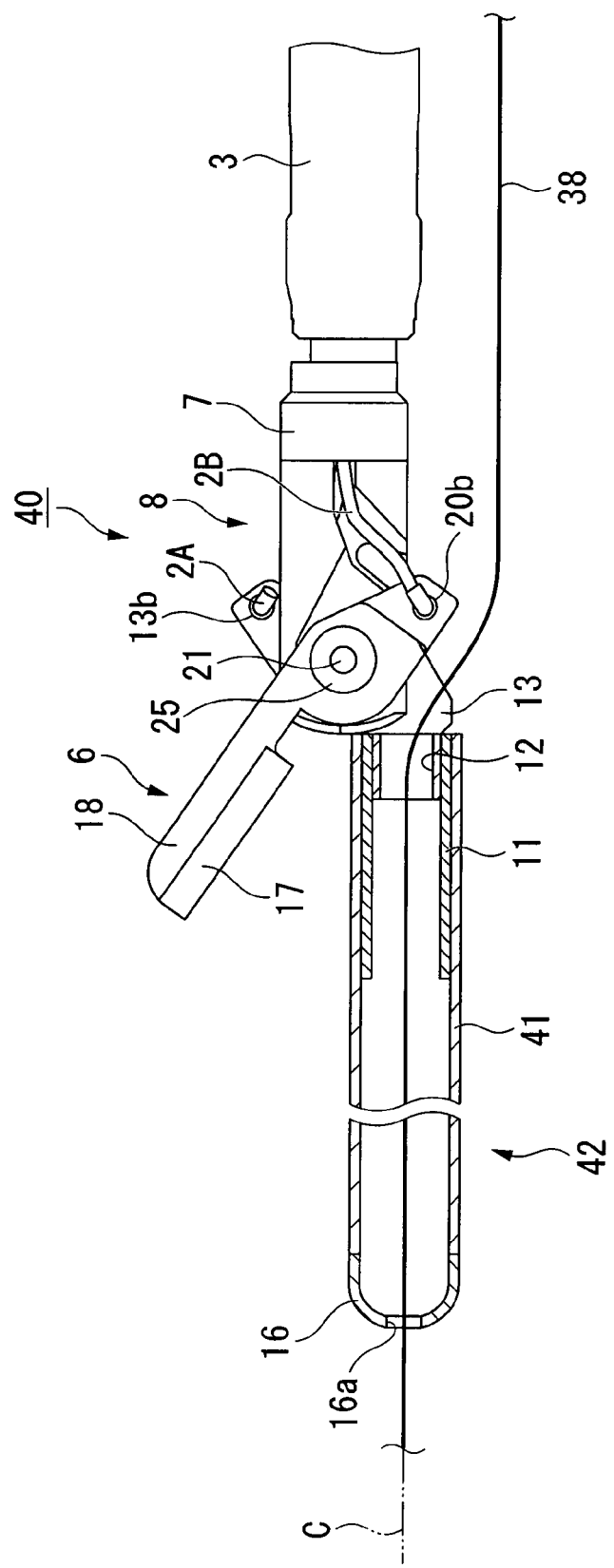
FIG. 5 is an essential component side view that includes a cross-section through a portion of the soft bipolar forceps according to the second embodiment of the present invention.

Next, a second embodiment of the invention will be explained with reference to FIG. 5.

Note that compositional elements that are equivalent to those of the first embodiment have been assigned the same numeric symbols, and a description thereof is omitted.

The difference between the first and second embodiments is that the guide part 41 of the soft bipolar forceps 40 according to the second embodiment is a tube that has both conductive properties and pliability.

The guide part 41 has conductivity through the use of carbon, for example, and engages with the outer peripheral surface of the front end side of the first arm 12 of the forceps piece 42. An end tip 16 is provided to the distal end of the guide part 41.

Actions and effects equivalent to those of the first embodiment can be achieved using this soft bipolar forceps 40. In particular, since a tube instead of a coil member is employed for the guide part 41, the guide part 41 can be smoothly inserted into the papilla 36.

Figure 6:
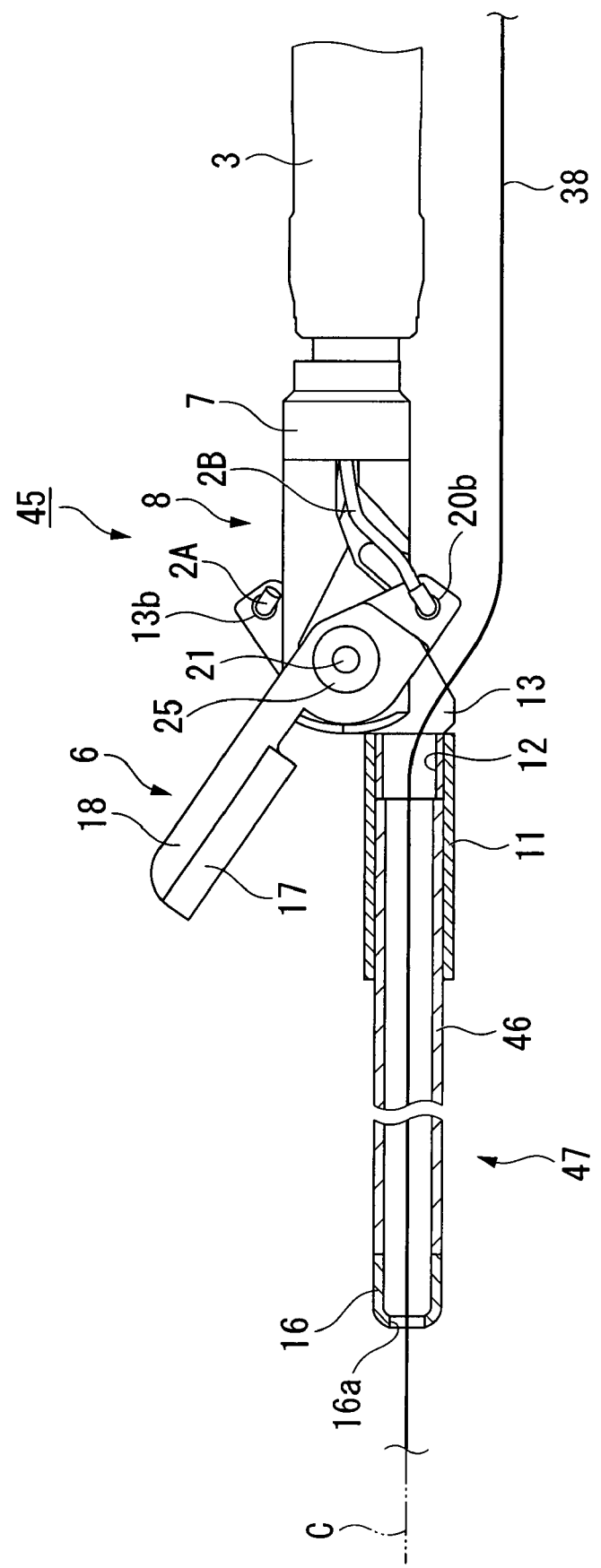
FIG. 6 is an essential component side view that includes a cross-section through a portion of the soft bipolar forceps according to the third embodiment of the present invention.

Next, a third embodiment of the invention will be explained with reference to FIG. 6.

Note that compositional elements that are equivalent to those of the other embodiments have been assigned the same numeric symbols, and a description thereof is omitted.

The second and third embodiments differ from one another in that the guide part 46 of the soft bipolar forceps 45 according to this embodiment is a tube that possesses both insulating properties and pliability.

The guide part 46 consists of a resin, for example, and engages with the outer peripheral surface of the front end side of the first arm 12 of the forceps piece 47 in the same manner as in the second embodiment.

Next, the operation of the soft bipolar forceps 45 according to this embodiment will be explained.

First, as in the case of the first embodiment, the diseased area that is to be incised is gripped by the paired forceps pieces 47, 6.

Electrical energy is supplied to the first electrode 11 and the second electrode 17 via the paired operating wires 2A, 2B through the activation of the high-frequency power source, so that current flows through the diseased area held between the paired forceps pieces 47, 6, causing cutting. In contrast, current does not flow through the biological tissue that is in contact with the guide part 46, so cutting does not occur.

This soft bipolar forceps 45 enables current to flow only though the part that is gripped between the first electrode 11 and the second electrode 17.

Figure 7:
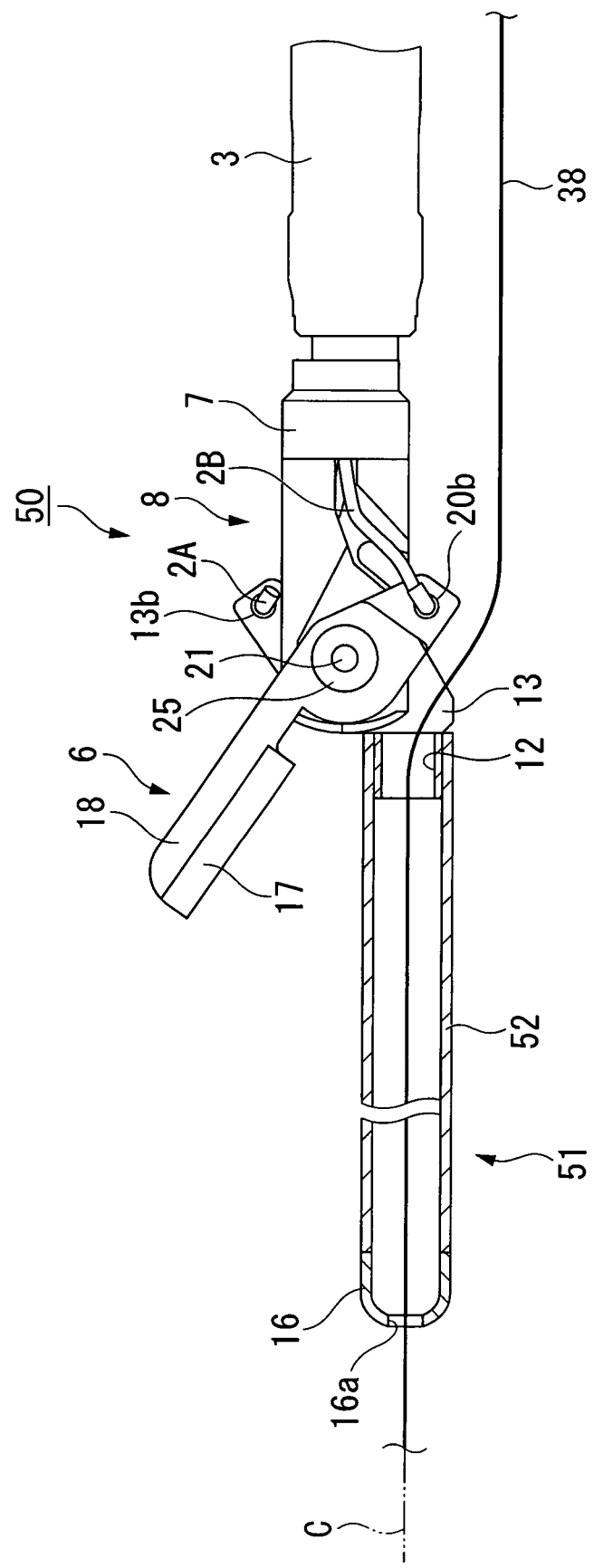
FIG. 7 is an essential component side view that includes a cross-section through a portion of the soft bipolar forceps according to the forth embodiment of the present invention.

Next, the fourth embodiment will be explained with reference to FIG. 7.

Note that compositional elements that are equivalent to those of the other embodiments have been assigned the same numeric symbols, and a description thereof is omitted.

The difference between the forth and first embodiments is that the first electrode 52 of the forceps piece 51 in the soft bipolar forceps 50 according to the forth embodiment is elastically deformable and is formed in a unitary manner with the guide part 41 according to the second embodiment.

Namely, the first electrode 52 forms the guide part and is disposed extending toward the front end of the forceps piece 51.

In this soft bipolar forceps 50, the diseased area can be incised in the same manner as in the preceding embodiments, by gripping the diseased area between the paired forceps pieces 51, 6. In particular, it is possible to insert only a pliable component since there is no rigid portion in the inserted part.

Note that the technical scope of the present invention is not limited to the above-described embodiments. Rather, various modifications are possible so long as they do not depart from the spirit of the invention.

For example, in the preceding embodiments, the paired forceps pieces are insulated by means of an insulating spacer 25 that is disposed to the tip cover 8. However, instead of this insulating spacer 25, it is also acceptable to provide an insulating coating to the base end of the paired forceps pieces as the insulating part. In this case, it is possible to have direct insulation between the forceps pieces.

Further, in the preceding embodiments, the guide part and the first electrode extend linearly, however it is also acceptable to form them in a curved shape with a pre-determined curving rate.

The present invention enables a target body tissue to be easily incised while being held stably between paired forceps pieces, and permits shortening of the procedure time. The incision of the subject tissue is performed by transmitting a current between the first electrode and the second electrode when the subject tissue is held between the paired forceps pieces. In this case, when the subject tissue is tubular for example, it is possible to position one of the forceps pieces with respect to the subject tissue by inserting the guide part into the subject tissue, and to grip the wall of the tube stably between the paired forceps pieces.

The present invention also enables the insertion of the instruments required for the procedure into the through hole, and enables movement of the instruments via the through hole. It is possible to further increase the axial length of the elastically deformable part, facilitating insertion into a tubular space.

Because there is a state of conductivity between the guide part and the first electrode, it is possible for current to flow between the guide part and the second electrode in the present invention. The present invention also enables the electrical insulation between the paired forceps pieces at the support to be suitably maintained by the insulating part. As a result, electrical insulation of both paired forceps pieces can be suitably maintained even if their base ends come into direct contact.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A soft bipolar forceps comprising:
 a long narrow flexible tube;
 a pair of forceps pieces that are formed extending in the axial direction, and are mutually insulated and disposed opposite one another;
 a support that is disposed to a distal end of said flexible tube and supports said paired forceps pieces to permit relatively free opening and closing thereof;
 a first electrode that is disposed on one of said paired forceps pieces;
 a second electrode that is disposed on the other of said paired forceps pieces opposite said first electrode; and
 a guide part that extends distally from a distal end of the first electrode and is formed so as to permit elastic deformation of the guide part.

2. A soft bipolar forceps according to claim 1, a through hole is provided in the axial direction of said guide part.

3. A soft bipolar forceps according to claim 1 or claim 2, said guide part is provided with conductive properties.

4. A soft bipolar forceps according to claim 3, said first electrode is formed in a unitary manner with said guide part in a manner that enables elastic deformation of both the first electrode and the guide part.

5. A soft bipolar forceps according to claim 1, an insulating part for electrically insulating between said paired forceps pieces is disposed to said support.

6. A soft bipolar forceps according to claim 1, further comprising an insulating part which electrically insulates between said paired forceps pieces and is disposed to respective base ends of said paired forceps pieces.

\* \* \* \* \*